US011208666B2

(12) United States Patent
Brandon et al.

(10) Patent No.: US 11,208,666 B2
(45) Date of Patent: Dec. 28, 2021

(54) MUTANT XYLAN BIOSYNTHETIC ENZYMES CAPABLE OF DOMINANT SUPPRESSION OF XYLAN BIOSYNTHESIS

(71) Applicant: The Regents of the University of California, Oakland, CA (US)

(72) Inventors: Andrew Brandon, Berkeley, CA (US); Henrik Vibe Scheller, Millbrae, CA (US); Dominique Loque, Vernier (CH)

(73) Assignee: The Regents of the University of California, Oakland, CA (US)

( * ) Notice: Subject to any disclaimer, the term of this patent is extended or adjusted under 35 U.S.C. 154(b) by 351 days.

(21) Appl. No.: 15/847,788

(22) Filed: Dec. 19, 2017

(65) Prior Publication Data

US 2018/0251774 A1    Sep. 6, 2018

Related U.S. Application Data

(60) Provisional application No. 62/435,687, filed on Dec. 16, 2016.

(51) Int. Cl.
| | | |
|---|---|---|
| *C12N 15/82* | (2006.01) | |
| *C07K 14/415* | (2006.01) | |
| *C12N 9/10* | (2006.01) | |

(52) U.S. Cl.
CPC ........ *C12N 15/8216* (2013.01); *C07K 14/415* (2013.01); *C12N 9/1077* (2013.01); *C12N 15/8202* (2013.01); *C12N 15/8246* (2013.01)

(58) Field of Classification Search
CPC ............ C12N 15/8218; C12N 15/8216; C12N 15/8246
See application file for complete search history.

(56) References Cited

U.S. PATENT DOCUMENTS

2017/0107542 A1*  4/2017  Mohnen ............... C12Y 204/02

OTHER PUBLICATIONS

Wu, Ai-Min, et al. "The *Arabidopsis* IRX10 and IRX10-LIKE glycosyltransferases are critical for glucuronoxylan biosynthesis during secondary cell wall formation." The Plant Journal 57.4 (2009): 718-731. (Year: 2009).*
Wu et al (2009, "The *Arabidopsis* IRX10 and IRX10-LIKE Glycosyltransferases are Critical for Glucuronoxylan Biosynthesis during Secondary Cell Wall Formation", The Plant Journal 57:718-731).*
Bowie et al, (1990, "Deciphering the Message in Protein Sequences: Tolerance to Amino Acid written Substitutions", Science 247: 1306-1310).*
McConnell et al, (2001, "Radial Patterning of *Arabidopsis* Shoots By Class III HD-ZIP and KANADI Genes", Nature 411 (6838):709-713).*
Kano-Murakami et al (1993, "A Rice Homeotic Gene, OSH1, Causes Unusual Phenotypes in Transgenic Tobacco", FEBS 334:365-368).*
Lao et al (2020, NCBI Accession No. Q9FZJ1).*
Brandon, et al., "Dominant suppression of xylan biosynthesis using IRX10." Joint BioEnergy Institute and Biological Systems and Engineering Division, Lawrence Berkeley National Laboratory, Berkeley, CA 94720, USA. Poster submission Dec. 16, 2016 at: International Conference on Plant Synthetic Biology and Bioengineering (ICPSBB) 2016. https://www.aiche.org/sbe/conferences/international-conference-on-plant-synthetic-biology-and-bioengineering/2016/.
Lincoln et al., "A knotted1-like Homeobox Gene in *Arabidopsis* is Expressed in the Vegetative Meristem and Dramatically Alters Leaf Morphology When Overexpressed in Transgenic Plants. American Society of Plant Physiologists." The Plant Cell, vol. 6, 1859-1876 (1994).
Busk et al., "In Vivo Footprinting of Plant Tissues." Plant Molecular Biology Reporter, vol. 20, pp. 287-297 (2002).
Matsuoka et al., "The promoters of two carboxylases in a C4 plant (maize) direct cell-specific, light-regulated expression in a C3 plant (rice)." The Plant Journal, vol. 6, No. 3, pp. 311-319 (1994).
Bezerra et al., "A corm-specific gene encodes tarin, a major globulin of taro (*Colocasia esculenta* L. *Schott*)." Plant Molecular Biology, vol. 28, pp. 137-144 (1995).
Kim et al., "Nuclear protein factors binding to a class I patatin promoter region are tuber-specific and sucrose-inducible." Plant Molecular Biology vol. 26, pp. 603-615 (1994).
Altschul et al., "Gapped BLAST and PSI-BLAST: a new generation of protein database search programs." Oxford University Press Nucleic Acids Research, vol. 25, No. 17 , pp. 3389-3402 (1997).
Smith et al., "Comparison of Biosequences." Advances in Applied Mathematics, vol. 2, pp. 482-489 (1981).
Needleman et al., "A General Method Applicable to the Search for Similarities in the Amino Acid Sequence of Two Proteins." J. Mol. Biol., vol. 48, pp. 443-453 (1970).
Enjuto et al., "Expression of the *Arabidopsis* HMG2 Gene, Encoding 3-Hydroxy-3-Methylglutaryl Coenzyme A Reductase, 1s Restricted to Meristematic and Floral Tissues." American Society of Plant Physiologists, The Plant Cell, vol. 7, pp. 517-527, May 1995.
Li et al., "A novel myb-related gene from *Arabidopsis thaliana*." School of Botany and Centre for Protein and Enzyme Technology, La Trobe University, Bundoora, Melbourne, Victoria. Australia. FEBS Letters, vol. 379, pp. 117-121 (1996).
Meier et al., "Real-time detection of central carbon metabolism in living *Escherichia coli* and its response to perturbations." FEBS Letters, vol. 585, pp. 3133-3138 (2011).
Hansen et al., "Wound-inducible and organ-speci® c expression of ORF13 from Agrobacterium rhizogenes 8196 T-DNA in transgenic tobacco plants." Springer-Verlag, Mol Gen Genet, vol. 254, pp. 337-343 (1997).

(Continued)

*Primary Examiner* — Vinod Kumar
(74) *Attorney, Agent, or Firm* — Robin C. Chiang; Lawrence Berkeley National Laboratory

(57) ABSTRACT

The present invention provides for a polypeptide capable of dominant suppression of a first naturally occurring IRX10, wherein the polypeptide comprises an amino acid sequence having at least 70% identity as compared to a second naturally occurring IRX10 wherein the polypeptide comprises one or more of the conserved amino acid indicated in FIG. 2 substituted with a different amino acid residue.

11 Claims, 4 Drawing Sheets

Specification includes a Sequence Listing.

(56) References Cited

OTHER PUBLICATIONS

Sambrook, "Molecular Cloning: A Laboratory Manual, Third Edition (3 volume set)" QF-22862 US/Data/Medical-Books. Uploaded: Jul. 10, 2018 http://eaststemcell.com/files/storage.cloud.php?id=MDg3OTY5NTc3Mw==.

Altschul et al, "Basic Local Alignment Search Tool." J. Mol. Biol.., vol. 215, pp. 403-410 (1990).

Hake et al., "Homeobox genes in the functioning of plant meristems." Phil. Trans. R. Soc. Lond. B., vol. 350, pp. 45-51 (1995). Downloaded Jun. 12, 2018 from http://rstb.royalsocietypublishing.org/.

Long et al., "A member of the KNOTTED Class of homeodomain proteins encoded by the STM gene *Arabidopsis*." Letters to Nature, Dept of Genetics, and Program in Cellular and Molecular Biology, Univ of Wisconsin, Madison, WI., 53706 USA, vol. 379, No. 4, pp. 66-69 (1996).

Casal et al, "Different Phototransduction Kinetics of Phytochrome A and Phytochrome B in *Arabidopsis thaliana*1." Plant Physiol., vol. 116, pp. 1533-1538 (1998).

Yamamoto et al., "Characterization of cís-Acting Sequences Regulating Root-Specific Gene Expression in Tobacco." American Society of Plant Physiologists, The Plant Cell, vol. 3, pp. 371-382, (1991).

Martin et al., "Identification of mutants in metabolically regulated gene expression." The Plant Journal vol. 1, No. 11, pp. 53-62 (1997).

Karlin et al., "Methods for assessing the statistical significance of molecular sequence features by using general scoring schemes." Evolution, Proc. Natl. Acad. Sci. USA vol. 87, pp. 2264-2268 (1990).

Pearson et al., "Improved tools for biological sequence comparison." Biochemistry, Proc. Natl. Acad. Sci. USA vol. 85, pp. 2444-2448 (1988).

Kerstetter et al., "Sequence Analysis and Expression Patterns Divide the Maize knotted-like Homeobox Genes into Two Classes." American Society of Plant Physiologists, The Plant Cell, vol. 6, pp. 1877-1887 (1994).

Dilaurenzio et al., "The SCARECROW Gene Regulates an Asymmetric Cell Division That is Essential for Generating the Radial Organization of the *Arabidopsis* Root." Cell Press, Cell, vol. 86, pp. 423-433 (1996).

Shiina et al., "Identification of Promoter Elements Involved in the Cytosolic Ca2+-Mediated Photoregulation of Maize cab-ml Expression." Plant Physiol., vol. 1, No. 5, pp. 477-483 (1997).

Decastro et al., "Spatial and Temporal Gene Expression Patterns Occur during Corm Development." American Society of Plant Physiologists, The Plant Cell, vol. 4, pp. 1549-1559, (1992).

Ausubel et al., "Current Protocols in Molecular Biology." John Wiley & Sons Inc; ringbou edition (2003). ISBN: 047150338X.

Henikoff et al., "Amino acid substitution matrices from protein blocks." Biochemistry, Proc. Natl. Acad. Sci. USA vol. 89, pp. 10915-10919 (1992).

* cited by examiner

MUTANT XYLAN BIOSYNTHETIC ENZYMES CAPABLE OF DOMINANT SUPPRESSION OF XYLAN BIOSYNTHESIS

CROSS-REFERENCE TO RELATED APPLICATIONS

This application claims priority to U.S. Provisional Patent Application Ser. No. 62/435,687, filed on Dec. 16, 2016, which is hereby incorporated by reference.

STATEMENT OF GOVERNMENTAL SUPPORT

The invention was made with government support under Contract No. DE-AC02-05CH11231 awarded by the U.S. Department of Energy. The government has certain rights in the invention.

FIELD OF THE INVENTION

The present invention is in the field of xylan biosynthesis in plants.

BACKGROUND OF THE INVENTION

Xylan is the most abundant non-cellulosic polysaccharide in plant biomass and one of the most abundant biopolymers on earth. The xylan backbone is a homopolymer of β-(1,4)-linked xylose, decorated at regular intervals with GlcA, 4-O-MeGlcA and acetyl groups. As a hemicellulose, xylan is thought to coat and crosslink cellulose microfibrils, promoting their crystallinity. Indeed, xylan is critical for the overall health and mechanical strength of the plant. Xylan biosynthesis mutants are severely dwarfed due to cell wall collapse in the water-conducting xylem vessels. While important, the relatively high amount of xylan in plant biomass creates several problems for the development of advanced biofuels. Xylose, a 5-carbon sugar, is poorly utilized by microorganisms and strongly inhibits the fermentation of 6-carbon sugars like glucose. Additionally, the acetate released from the xylan backbone creates a toxic environment for microbial growth. Any way to reduce the amount of xylan in plant biomass could have a significant effect on the conversion efficiency to biofuel. Since few, if any, mutants of biotechnologically relevant crops exist, the ideal approach would act as a dominant suppressor of xylan biosynthesis.

SUMMARY OF THE INVENTION

The present invention provides for a polypeptide capable of dominant suppression of a first naturally occurring IRX10, wherein the polypeptide comprises an amino acid sequence having at least 70% identity as compared to a second naturally occurring IRX10 wherein the polypeptide comprises one or more of the conserved amino acid indicated in FIG. 2 substituted with a different amino acid residue. The conserved amino acid residues are the ones which are identical for IRX10, IRX10-L, OsIRX10, PpIRX10, as indicated in FIG. 2. In some embodiments, the conserved amino acid residue is indicated by an asterisk in FIG. 2. In some embodiments, the first naturally occurring IRX10 and the second naturally occurring IRX10 are the same IRX10.

In some embodiments, the conserved amino acid residue corresponds to the histidine at position 146, the phenylalanine at position 277, the cysteine at position 278, the glycine at position 283, or glutamate at position 293 of *Arabidopsis* IRX10. In some embodiments, the polypeptide has one or more of the following substitutions: H146D, F277A, C278A, G283D, or E293Q.

In some embodiments, the naturally occurring IRX10, for the first or second naturally occurring IRX10, or both, is *Arabidopsis* IRX10, IRX10-L, OsIRX10, PpIRX10, or HsEXO1.

This invention provides for a means to identify potential catalytic residues in the xylan biosynthetic enzyme IRX10 and mutating them. Overexpression of the mutated IRX10 outcompetes the native form of the enzyme, suppressing the biosynthesis of the polymer.

The present invention provides for a genetically modified eukaryotic host cell comprising (a) a gene encoding a polypeptide of the present invention operably linked to a promoter, wherein the gene and/or the promoter is heterologous to the cell. The host cell has a native IRX10. In some embodiment, the native IRX10 is disrupted. The modified cell is altered in producing xylan and produces modified cellulose and/or cell wall that comprises less xylan. In some embodiments, the host cell is a plant cell. In some embodiments, the host cell is part of a plant. In some embodiments, the host cell is a plant cell wherein all of the cells of the plant are similarly modified.

The present invention provides for a plant comprising the cell of the present invention, or a progeny thereof.

The present invention provides for a seed from the plant of the present invention.

The present invention provides for a biomass comprising plant tissue from the plant of the present invention.

The present invention provides for a method of obtaining a polypeptide of the present invention, comprising: (a) providing a nucleic acid encoding a naturally occurring IRX10, (b) introducing or generating a mutation into an open reading frame (ORF) encoding the naturally occurring IRX10 which results in an amino acid substitution of a conserved amino acid residue, as indicated in FIG. 2, in the naturally occurring IRX10, (c) optionally introducing the nucleic acid into a eukaryotic host cell, and (d) optionally culturing or growing the eukaryotic host cell.

In some embodiments, the method results in a decrease of the amount of xylan in a plant comprising the plant cell.

In some embodiments, host cell is part of a plant and the method further comprises: collecting plant material from the plant, and optionally incubating the plant material from the plant in a saccharification reaction.

The present invention provides for a method of improving the amount of soluble sugar obtained from a plant biomass material, comprising: (a) providing plant biomass material from a plant which expresses the polypeptide of the present invention, (b) performing a saccharification reaction on the plant biomass material, and (c) obtaining soluble sugar.

The present invention provides for a saccharification reaction comprising grass plant biomass material from a plant which expresses the polypeptide of the present invention.

The present invention provides for a method of engineering a plant to increase the content of a sugar in a desired tissue, comprising: (a) introducing an expression cassette into the plant, wherein the expression cassette comprises a polynucleotide encoding the polypeptide of the present invention operably linked to a heterologous promoter, and (b) culturing the plant under conditions in which the polypeptide is expressed in the desired tissue; wherein the heterologous promoter specifically expresses in the desired tissue. In some embodiments, the desired tissue is plant vessel tissue.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION OF THE INVENTION

Figure 1:
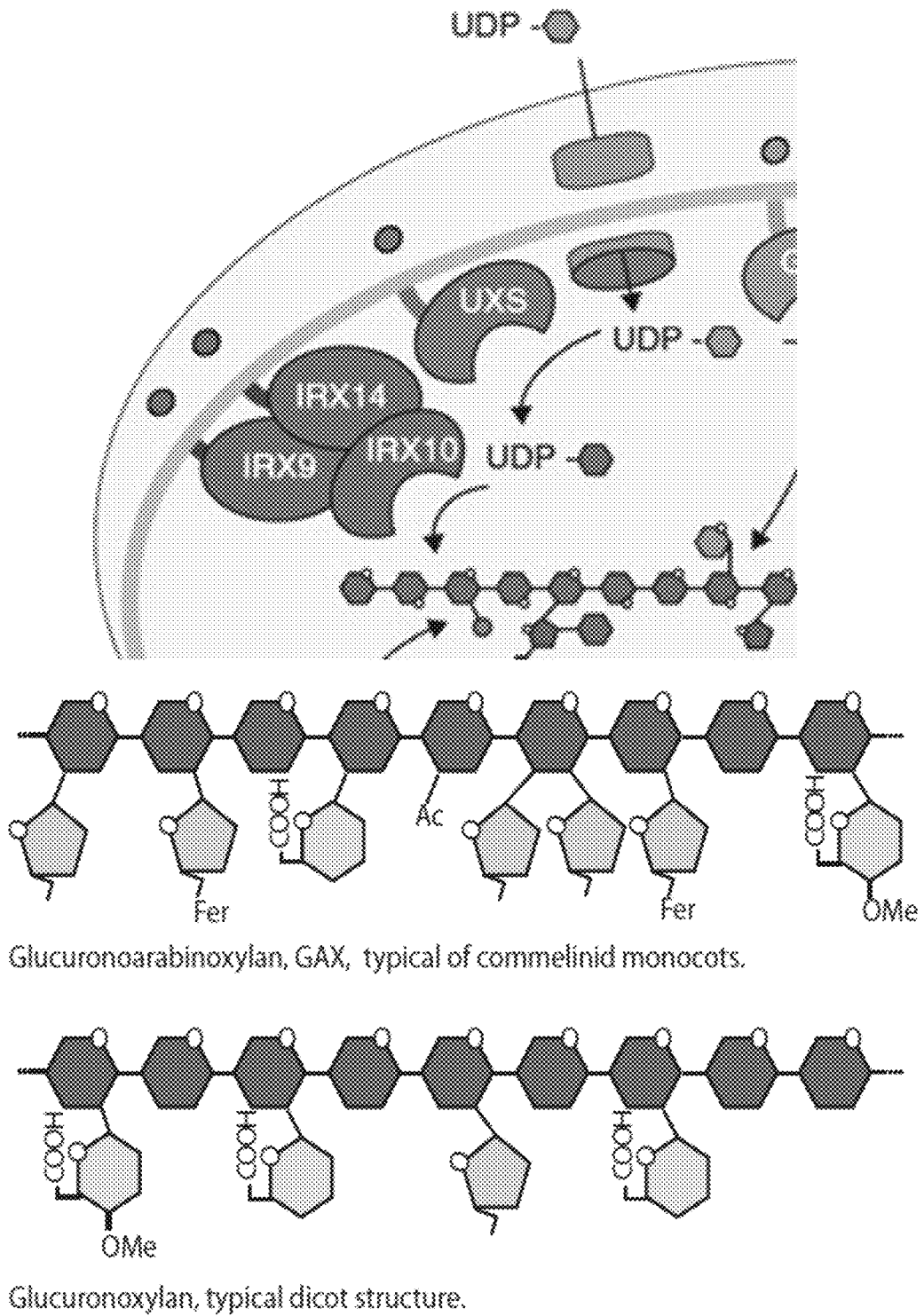
FIG. 1 shows the function of IRX10 in the synthesis of cellulose.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The terms "polynucleotide" and "nucleic acid" are used interchangeably and refer to a single or double-stranded polymer of deoxyribonucleotide or ribonucleotide bases read from the 5' to the 3' end. A nucleic acid of the present invention will generally contain phosphodiester bonds, although in some cases, nucleic acid analogs may be used that may have alternate backbones, comprising, e.g., phosphoramidate, phosphorothioate, phosphorodithioate, or O-methylphophoroamidite linkages (see Eckstein, Oligonucleotides and Analogues: A Practical Approach, Oxford University Press); positive backbones; non-ionic backbones, and non-ribose backbones. Thus, nucleic acids or polynucleotides may also include modified nucleotides that permit correct read-through by a polymerase. "Polynucleotide sequence" or "nucleic acid sequence" includes both the sense and antisense strands of a nucleic acid as either individual single strands or in a duplex. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc.

Two nucleic acid sequences or polypeptide sequences are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11-17 (1988) e.g., as implemented in the program PC/GENE (Intelligenetics, Mountain View, Calif., USA).

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

Algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1977) *Nucleic Acids Res.* 25: 3389-3402, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad. Sci. USA* 89:10915 (1989)).

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about $10^{-5}$, and most preferably less than about $10^{-20}$.

Nucleic acid or protein sequences that are substantially identical to a reference sequence include "conservatively modified variants." With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are illustrative conservative substitutions for one another: (1) Alanine (A), Serine (S), Threonine (T); (2) Aspartic acid (D), Glutamic acid (E); (3) Asparagine (N), Glutamine (Q); (4) Arginine (R), Lysine (K); (5) Isoleucine (I), Leucine (L), Methionine (M), Valine (V); and (6) Phenylalanine (F), Tyrosine (Y), Tryptophan (W). (see, e.g., Creighton, *Proteins* (1984)).

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C. For example, stringent conditions for hybridization, such as RNA-DNA hybridizations in a blotting technique are those which include at least one wash in 0.2×SSC at 55° C. for 20 minutes, or equivalent conditions.

The term "promoter," as used herein, refers to a polynucleotide sequence capable of driving transcription of a DNA sequence in a cell. Thus, promoters used in the polynucleotide constructs of the invention include cis- and trans-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) gene transcription. Promoters are located 5' to the transcribed gene, and as used herein, include the sequence 5' from the translation start codon (i.e., including the 5' untranslated region of the mRNA, typically comprising 100-200 bp). Most often the core promoter sequences lie within 1-2 kb of the translation start site, more often within 1 kbp and often within 500 bp of the translation start site. By convention, the promoter sequence is usually provided as the sequence on the coding strand of the gene it controls. In the context of this application, a promoter is typically referred to by the name of the gene for which it naturally regulates expression. A promoter used in an expression construct of the invention is referred to by the name of the gene. Reference to a promoter by name includes a wildtype, native promoter as well as variants of the promoter that retain the ability to induce expression. Reference to a promoter by name is not restricted to a particular species, but also encompasses a promoter from a corresponding gene in other species.

A "constitutive promoter" in the context of this invention refers to a promoter that is capable of initiating transcription in nearly all cell types, whereas a "cell type-specific promoter" or "tissue-specific promoter" initiates transcription only in one or a few particular cell types or groups of cells forming a tissue (for a multi-cellular organism). In some embodiments, a plant promoter is tissue-specific if the transcription levels initiated by the promoter in the cell wall are at least 2-fold, 3-fold, 4-fold, 5-fold, 6-fold, 7-fold, 8-fold, 9-fold, 10-fold, 50-fold, 100-fold, 500-fold, 1000-fold higher or more as compared to the transcription levels initiated by the promoter in non-cell wall tissues A polynucleotide is "heterologous" to an organism or a second polynucleotide sequence if it originates from a foreign species, or, if from the same species, is modified from its original form. For example, when a polynucleotide encoding a polypeptide sequence is said to be operably linked to a heterologous promoter, it means that the polynucleotide coding sequence encoding the polypeptide is derived from one species whereas the promoter sequence is derived from another, different species; or, if both are derived from the same species, the coding sequence is not naturally associated with the promoter (e.g., is a genetically engineered coding sequence, e.g., from a different gene in the same species, or an allele from a different ecotype or variety).

The term "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a DNA or RNA sequence if it stimulates or modulates the transcription of the DNA or RNA sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The term "expression cassette" or "DNA construct" or "expression construct" refers to a nucleic acid construct that, when introduced into a host cell, results in transcription and/or translation of an RNA or polypeptide, respectively. Antisense or sense constructs that are not or cannot be translated are expressly included by this definition. In the case of both expression of transgenes and suppression of endogenous genes (e.g., by antisense, RNAi, or sense suppression) one of skill will recognize that the inserted polynucleotide sequence need not be identical, but may be only substantially identical to a sequence of the gene from which it was derived. As explained herein, these substantially identical variants are specifically covered by reference to a specific nucleic acid sequence. One example of an expression cassette is a polynucleotide construct that comprises a polynucleotide sequence encoding a protein operably linked to a heterologous promoter. In some embodiments, an expression cassette comprises a polynucleotide sequence encoding a protein that is targeted to a position in a plant genome such that expression of the polynucleotide sequence is driven by a promoter that is present in the plant The term "plant" as used herein can refer to a whole plant or part of a plant, e.g., seeds, and includes plants of a variety of ploidy levels, including aneuploid, polyploid, diploid and haploid. The term "plant part," as used herein, refers to shoot vegetative organs and/or structures (e.g., leaves, stems and tubers), branches, roots, flowers and floral organs (e.g., bracts, sepals, petals, stamens, carpels, anthers), ovules (including egg and central cells), seed (including zygote, embryo, endosperm, and seed coat), fruit (e.g., the mature ovary), seedlings, and plant tissue (e.g., vascular tissue, ground tissue, and the like), as well as individual plant cells, groups of plant cells (e.g., cultured plant cells), protoplasts, plant extracts, and seeds. The class of plants that can be used in the methods of the invention is generally as broad as the class of higher and lower plants amenable to transformation techniques, including angiosperms (monocotyledonous and dicotyledonous plants), gymnosperms, ferns, bryophytes, and multicellular algae.

The term "biomass," as used herein, refers to plant material that is processed to provide a product, e.g., a biofuel such as ethanol, or livestock feed, or a cellulose for paper and pulp industry products. Such plant material can include whole plants, or parts of plants, e.g., stems, leaves, branches, shoots, roots, tubers, and the like.

The term "saccharification reaction" refers to a process of converting biomass, usually cellulosic or lignocellulosic biomass, into monomeric sugars, such as glucose and xylose.

The term "soluble sugar" refers to monomeric, dimeric, or trimeric sugar that is produced from the saccharification of biomass.

The term "increased amount," when referring to an amount of sugar or soluble sugar obtained from an engineered plant of the present invention, refers to an increase in the amount or yield of sugar that is obtained from saccharification of biomass per amount of starting material, in comparison to corresponding biomass from a wild-type (i.e., naturally occurring) plant. In the context of the present invention, "corresponding biomass from a wild-type plant" refers to plant material that is from the same part of the plant as the biomass from a plant engineered to have modified sugar levels. As understood in the art, increased amount or increased yield is based upon comparisons of the same amount of corresponding plant material.

The term "conversion reaction," as used herein, refers to a reaction that converts biomass into a form of bioenergy. Examples of conversion reactions include, but are not limited to, combustion (burning), gasification, pyrolysis, and polysaccharide hydrolysis (enzymatic or chemical).

The term "increased production," when referring to an amount of bioenergy production obtained from an engineered plant of the present invention, refers to an increased amount of bioenergy that is produced from subjecting biomass from an engineered plant to a conversion reaction (e.g., combustion, gasification, pyrolysis, or polysaccharide hydrolysis) as compared to the amount of bioenergy that is produced from corresponding biomass from a wild-type (i.e., naturally occurring) plant.

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

These and other objects, advantages, and features of the invention will become apparent to those persons skilled in the art upon reading the details of the invention as more fully described below.

This invention is useful for engineering bioenergy plants with a cell wall composition that makes their sugars easier accessible. This will be interesting for a variety of industries, such as biofuel production or sugar producing industries. Likewise, the invention could be useful for developing plants for other purposes, such as for feed and forage.

In one aspect, the invention provides a method of engineering plants to decrease xylan content. Eukaryotic cells can be engineered to overexpress one or more polypeptide in a cell by genetically modifying the cell to overexpress one or more polypeptide genes as described herein. In some embodiments, plants can be engineered to overexpress express one or more polypeptide in the plant by genetically modifying the plant to overexpress one or more polypeptide genes as described herein. Typically, overexpression is targeted to cell wall using a tissue-specific promoter. An example of a method for fine-tuning gene expression to increase expression in the cell wall is taught in PCT/US2012/023182, which is incorporated by reference.

The invention employs various routine recombinant nucleic acid techniques. Generally, the nomenclature and the laboratory procedures in recombinant DNA technology described below are those well known and commonly employed in the art. Many manuals that provide direction for performing recombinant DNA manipulations are available, e.g., Sambrook & Russell, Molecular Cloning, A Laboratory Manual (3rd Ed, 2001); and Current Protocols in Molecular Biology (Ausubel, et al., John Wiley and Sons, New York, 2009).

In some embodiments, the IRX10 is an IRX10 of *Arabidopsis*, poplar, eucalyptus, rice, corn, cotton, switchgrass, sorghum, millet, miscanthus, sugarcane, pine, alfalfa, wheat, soy, barley, turfgrass, tobacco, hemp, bamboo, rape, sunflower, willow, or *Brachypodium*.

The amino acid sequence of *Arabidopsis thaliana* IRX10 is as follows:

```
                                              (SEQ ID NO: 1)
           10         20         30         40
    MKIHSCLSAI LLFLFFSASS AKQNVRTERI SGSAGDVLED 50         60         70         80
    DPVGKLKVYV YELPSKYNKK LLQKDPRCLT HMFAAEIFMH 90        100        110        120
    RFLLSSPVRT RNPDEADWFY TPIYPTCDLT PTGLPLPFKS 130        140        150        160
    PRMMRSSIQL ISSNWPYWNR TEGADHFFVV PHDFGACFHY 170        180        190        200
    QEEKAIERGI LPLLQRATLV QTFGQRNHVC LDEGSITIPP 210        220        230        240
    FAPPQKMQAH FIPPDIPRSI FVYFRGLFYD VNNDPEGGYY 250        260        270        280
    ARGARAAVWE NFKNNPLFDI STDHPTTYYE DMQRAIFCLC 290        300        310        320
    PLGWAPWSPR LVEAVVFGCI PVIIADDIVL PFADAIPWEE 330        340        350        360
    IGVFVAEKDV PELDTILTSI PTEVILRKQR LLANPSMKRA 370        380        390        400
    MLFPQPAQPG DAFHQILNGL ARKLPHDKSI YLKTGEKALN

410
    WTAGPVADLK PW
```

The amino acid sequence of *Arabidopsis thaliana* IRX10L is as follows:

```
                                              (SEQ ID NO: 2)
           10         20         30         40
    MKLSSCVLIF LLCNTFSSIS AFRLSRSQPT ERISGSAGDV 50         60         70         80
    LEDDPVGRLK VFVYELPSKY NKKILQKDPR CLNHMFAAEI 90        100        110        120
    YMQRFLLSSP VRTLNPEEAD WFYVPVYTTC DLTPNGLPLP 130        140        150        160
    FKSPRMMRSA IQLIASNWPY WNRTEGADHF FVVPHDFGAC 170        180        190        200
    FHYQEEKAIG RGILPLLQRA TLVQTFGQRN HVCLKEGSIT 210        220        230        240
    VPPYAPPQKM QSHLIPEKTP RSIFVYFRGL FYDVGNDPEG 250        260        270        280
    GYYARGARAA VWENFKDNPL FDISTEHPTT YYEDMQRAIF 290        300        310        320
    CLCPLGWAPW SPRLVEAVIF GCIPVIIADD IVLPFADAIP 330        340        350        360
    WEDIGVFVDE KDVPYLDTIL TSIPPEVILR KQRLLANPSM 370        380        390        400
    KQAMLFPQPA QPGDAFHQVL NGLARKLPHE RSVYLRPGEK

410
    LLNWTAGPVA DLKPW
```

The amino acid sequence of rice OsIRX10 (as known as Os01g70200) is as follows:

```
                                              (SEQ ID NO: 3)
    MRRWVLAIAILAAAVCFFLGAQAQEVRQGHQTERISGSAGDVLEDDPVGR

LKVYVYDLPSKYNKKLLKKDPRCLNHMFAAEIFMHRFLLSSAVRTFNPEE

ADWFYTPVYTTCDLTPSGLPLPFKSPRMMRSAIELIATNWPYWNRSEGAD

HFFVTPHDFGACFHYQEEKAIGRGILPLLQRATLVQTFGQKNHVCLKDGS
```

```
                                                            -continued
ITIPPYAPPQKMQAHLIPPDTPRSIFVYFRGLFYDTSNDPEGGYYARGAR

ASVWENFKNNPLFDISTDHPPTYYEDMQRSVFCLCPLGWAPWSPRLVEAV

VFGCIPVIIADDIVLPFADAIPWEEIGVFVAEEDVPKLDSILTSIPTDVI

LRKQRLLANPSMKQAMLFPQPAQAGDAFHQILNGLARKLPHGENVFLKPG

ERALNWTAGPVGDLKPW
```

The amino acid sequence of *Physcomitrella patens* IRX10 (PpIRX10) is as follows:

```
                                                    (SEQ ID NO: 4)
            10         20         30         40
      MEHPLECADS CSLAMSWFCN KKCRGWGLMK RTVVASGLRS 50         60         70         80
      VVLLLLFIYF VQDVTAEMGH QRISGSAGDV LEDNPVGRLK 90        100        110        120
      VFIYDIPSKY NTDWLKKDPR CLTHMFAVEE YLHDFLTESP 130        140        150        160
      VRTLNPEEAD WFYTPVYTTC DLTPNGLPLP FKSPRVMRSA 170        180        190        200
      ISYISSHWPY WNRTDGADHF FVVPHDFAAC FHYQEEKAIE 210        220        230        240
      RGILPLLKRA TLIQTFGQNH HVCLKEDSIV IPPYAPPERM 250        260        270        280
      QTRLNPPSTP RSIFAYFRGL FYDPGNDPEG GYYARGARAA 290        300        310        320
      IWENFKDNPL FDISTEHPAT YYEDMQRAIF CLCPLGWAPW 330        340        350        360
      SPRLVEGVIF GCIPVIIADD IVLPFADAIP WEKIGVFVEE 370        380        390        400
      KDVPILDKIL CTINHEEVLE KQRLLANPAM KQAMLFPRPA 410        420        430        440
      KPGDAFHQIL NGLARKLPHD PSIYLQPGQS FLNWTEGPPG

DLYPWGNDL
```

To use isolated sequences in the above techniques, recombinant DNA vectors suitable for transformation of plant cells such as crop plant cells are prepared. Techniques for transformation are well known and described in the technical and scientific literature. For example, a DNA sequence encoding the polypeptide can be combined with transcriptional and other regulatory sequences which will direct the transcription of the sequence from the gene in the intended cells, e.g., grass or other crop plant cells. In some embodiments, an expression vector that comprises an expression cassette that comprises the polypeptide gene further comprises a promoter operably linked to the polypeptide gene. In other embodiments, a promoter and/or other regulatory elements that direct transcription of the polypeptide gene are endogenous to the plant and an expression cassette comprising the polypeptide gene is introduced, e.g., by homologous recombination, such that the heterologous polypeptide gene is operably linked to an endogenous promoter and is expression driven by the endogenous promoter. Regulatory sequences include promoters, which may be either constitutive or inducible, or tissue-specific.

Tissue-Specific Promoters

In some embodiments, a plant promoter to direct expression of the polypeptide of the present invention in a specific tissue is employed (tissue-specific promoters). Tissue specific promoters are transcriptional control elements that are only active in particular cells or tissues at specific times during plant development, such as in vegetative tissues or reproductive tissues.

Examples of tissue-specific promoters under developmental control include promoters that initiate transcription only (or primarily only) in certain tissues, such as vegetative tissues, cell walls, including e.g., roots or leaves. A variety of promoters specifically active in vegetative tissues, such as leaves, stems, roots and tubers are known. For example, promoters controlling patatin, the major storage protein of the potato tuber, can be used (see, e.g., Kim, *Plant Mol. Biol.* 26:603-615, 1994; Martin, *Plant J.* 11:53-62, 1997). The ORF13 promoter from *Agrobacterium rhizogenes* that exhibits high activity in roots can also be used (Hansen, *Mol. Gen. Genet.* 254:337-343, 1997). Other useful vegetative tissue-specific promoters include: the tarn promoter of the gene encoding a globulin from a major taro (*Colocasia esculenta* L. Schott) corm protein family, tarin (Bezerra, *Plant Mol. Biol.* 28:137-144, 1995); the curculin promoter active during taro corm development (de Castro, *Plant Cell* 4:1549-1559, 1992) and the promoter for the tobacco root-specific gene TobRB7, whose expression is localized to root meristem and immature central cylinder regions (Yamamoto, Plant Cell 3:371-382, 1991).

Leaf-specific promoters, such as the ribulose biphosphate carboxylase (RBCS) promoters can be used. For example, the tomato RBCS1, RBCS2 and RBCS3A genes are expressed in leaves and light-grown seedlings, only RBCS1 and RBCS2 are expressed in developing tomato fruits (Meier, *FEBS Lett.* 415:91-95, 1997). A ribulose bisphosphate carboxylase promoters expressed almost exclusively in mesophyll cells in leaf blades and leaf sheaths at high levels (e.g., Matsuoka, *Plant J.* 6:311-319, 1994), can be used. Another leaf-specific promoter is the light harvesting chlorophyll a/b binding protein gene promoter (see, e.g., Shiina, *Plant Physiol.* 115:477-483, 1997; Casal, *Plant Physiol.* 116:1533-1538, 1998). The *Arabidopsis thaliana* myb-related gene promoter (Atmyb5) (Li, et al., *FEBS Lett.* 379:117-121 1996), is leaf-specific. The Atmyb5 promoter is expressed in developing leaf trichomes, stipules, and epidermal cells on the margins of young rosette and cauline leaves, and in immature seeds. Atmyb5 mRNA appears between fertilization and the 16 cell stage of embryo development and persists beyond the heart stage. A leaf promoter identified in maize (e.g., Busk et al., *Plant J.* 11:1285-1295, 1997) can also be used.

Another class of useful vegetative tissue-specific promoters are meristematic (root tip and shoot apex) promoters. For example, the "SHOOTMERISTEMLESS" and "SCARECROW" promoters, which are active in the developing shoot or root apical meristems, (e.g., Di Laurenzio, et al., *Cell* 86:423-433, 1996; and, Long, et al., Nature 379:66-69, 1996); can be used. Another useful promoter is that which controls the expression of 3-hydroxy-3-methylglutaryl coenzyme A reductase HMG2 gene, whose expression is restricted to meristematic and floral (secretory zone of the stigma, mature pollen grains, gynoecium vascular tissue, and fertilized ovules) tissues (see, e.g., Enjuto, Plant Cell. 7:517-527, 1995). Also useful are kn1-related genes from maize and other species which show meristem-specific expression, (see, e.g., Granger, *Plant Mol. Biol.* 31:373-378, 1996; Kerstetter, *Plant Cell* 6:1877-1887, 1994; Hake, Philos. Trans. R. Soc. Lond. B. Biol. Sci. 350:45-51, 1995).

For example, the *Arabidopsis thaliana* KNAT1 promoter (see, e.g., Lincoln, *Plant Cell* 6:1859-1876, 1994) can be used.

In some embodiments, the promoter is substantially identical to the native promoter of a promoter that drives expression of a gene involved in secondary wall deposition. Examples of such promoters are promoters from IRX1, IRX3, IRX5, IRX8, IRX9, IRX14, IRX7, IRX10, GAUT13, or GAUT14 genes. Specific expression in fiber cells can be accomplished by using a promoter such as the NST1 promoter and specific expression in vessels can be accomplished by using a promoter such as VND6 or VND7. (See, e.g., PCT/US2012/023182 for illustrative promoter sequences).

One of skill will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

Constitutive Promoters

A promoter, or an active fragment thereof, can be employed which will direct expression of a nucleic acid encoding a fusion protein of the invention, in all or most transformed cells or tissues, e.g. as those of a regenerated plant. Such promoters are referred to herein as "constitutive" promoters and are active under most environmental conditions and states of development or cell differentiation. Examples of constitutive promoters include those from viruses which infect plants, such as the cauliflower mosaic virus (CaMV) 35S transcription initiation region (see, e.g., Dagless, *Arch. Virol.* 142:183-191, 1997); the 1'- or 2'-promoter derived from T-DNA of *Agrobacterium tumefaciens* (see, e.g., Mengiste supra (1997); O'Grady, Plant Mol. Biol. 29:99-108, 1995); the promoter of the tobacco mosaic virus; the promoter of Figwort mosaic virus (see, e.g., Maiti, *Transgenic Res.* 6:143-156, 1997); actin promoters, such as the *Arabidopsis* actin gene promoter (see, e.g., Huang, *Plant Mol. Biol.* 33:125-139, 1997); alcohol dehydrogenase (Adh) gene promoters (see, e.g., Millar, *Plant Mol. Biol.* 31:897-904, 1996); ACT11 from *Arabidopsis* (Huang et al., *Plant Mol. Biol.* 33:125-139, 1996), Cat3 from *Arabidopsis* (GenBank No. U43147, Zhong et al., *Mol. Gen. Genet.* 251:196-203, 1996), the gene encoding stearoyl-acyl carrier protein desaturase from *Brassica napus* (Genbank No. X74782, Solocombe et al., *Plant Physiol.* 104:1167-1176, 1994), GPc1 from maize (GenBank No. X15596, Martinez et al., *J. Mol. Biol.* 208:551-565, 1989), Gpc2 from maize (GenBank No. U45855, Manjunath et al., *Plant Mol. Biol.* 33:97-112, 1997), other transcription initiation regions from various plant genes known to those of skill. See also Holtorf, "Comparison of different constitutive and inducible promoters for the overexpression of transgenes in *Arabidopsis thaliana*," *Plant Mol. Biol.* 29:637-646, 1995).

Inducible Promoters

In some embodiments, a plant promoter may direct expression of the nucleic acids under the influence of changing environmental conditions or developmental conditions. Examples of environmental conditions that may effect transcription by inducible promoters include anaerobic conditions, elevated temperature, drought or other environmental stress, or the presence of light. Examples of developmental conditions that may effect transcription by inducible promoters include senescence and embryogenesis. Such promoters are referred to herein as "inducible" promoters. For example, the invention can incorporate drought-specific promoter such as the drought-inducible promoter of maize (Busk et al., *Plant J,* 11: 1285-95, 1997); or alternatively the cold, drought, and high salt inducible promoter from potato (Kirch *Plant Mol. Biol.* 33:897-909, 1997).

Suitable promoters responding to biotic or abiotic stress conditions include the pathogen inducible PRP1-gene promoter (Ward et al., *Plant. Mol. Biol.* 22:361-366, 1993), the heat inducible hsp80-promoter from tomato (U.S. Pat. No. 5,187,267), cold inducible alpha-amylase promoter from potato (PCT Publication No. WO 96/12814) or the wound-inducible pinII-promoter (European Patent No. 375091). For other examples of drought, cold, and salt-inducible promoters, such as the RD29A promoter, see, e.g., Yamaguchi-Shinozalei et al., *Mol. Gen. Genet.* 236:331-340, 1993 are also known.

Alternatively, plant promoters which are inducible upon exposure to plant hormones, such as auxins, may be used to express the polypeptide gene. For example, the invention can use the auxin-response elements E1 promoter fragment (AuxREs) in the soybean (*Glycine max* L.) (Liu, *Plant Physiol.* 115:397-407, 1997); the auxin-responsive *Arabidopsis* GST6 promoter (also responsive to salicylic acid and hydrogen peroxide) (Chen, Plant J. 10: 955-966, 1996); the auxin-inducible parC promoter from tobacco (Sakai, 37:906-913, 1996); a plant biotin response element (Streit, *Mol. Plant Microbe Interact.* 10:933-937, 1997); and, the promoter responsive to the stress hormone abscisic acid (Sheen, *Science* 274:1900-1902, 1996).

In further embodiments, a plant can be engineered to overexpress the polypeptide using a positive feedback loop to express the polypeptide in a desired tissue. In some embodiments, a promoter for use in the polypeptide expression construct is responsive to a transcription factor that mediates expression in the desired tissue. The polypeptide expression construct is used in a genetically modified plant comprising an expression construct encoding a transcription factor where expression is also driven by a promoter that is responsive to the transcription factor. Examples of such expression systems are provided in PCT/US2012/023182, hereby incorporated by reference.

In some embodiments in which a positive feedback loop is employed, the plant is genetically modified to express a transcription factor that regulates the production of secondary cell wall. Examples of such transcription factors include NST1, NST2, NST3, SND2, SND3, MYB103, MBY85, MYB46, MYB83, MYB58, and MYB63 (See, e.g., Mitsuda et al., *Plant Cell* 17:2993-3006 (2005); Mitsuda et al., *Plant Cell* 19:270-80 (2007); Ohashi-Ito et al., *Plant Cell* 22:3461-73 (2010); Zhong et al., *Plant Cell* 20:2763-82 (2008); Zhong et al., *Plant Cell* 19:2776-92 (2007); Ko et al., *Plant J.* 60:649-65 (2009); and McCarthy et al., *Plant Cell Physiol.* 50:1950-64 (2009)). Illustrative examples of gene and protein sequences and/or accession numbers for NST1, NST2, NST3, SND2, SND3, MYB103, MBY85, MYB46, MYB83, MYB58, and MYB63 are provided in PCT/US2012/023182, hereby incorporated by reference.

In some embodiments, the polynucleotide encoding the transcription factor that regulates secondary cell wall production is operably linked to a promoter that is a downstream target of the transcription factor. Similarly, the polypeptide nucleic acid sequence is also linked to a promoter that is a downstream target of the transcription factor. The promoter may be the same promoter or different promoters. In such an embodiment, a promoter is suitable for use with the transcription factor that regulates secondary cell wall production if expression of the promoter is induced, directly or indirectly, by the transcription factor to be expressed, and if the promoter is expressed in the desired location, e.g., the stem of the plant.

In another embodiment, the polynucleotide encoding the polypeptide is expressed through a transposable element. This allows for constitutive, yet periodic and infrequent expression of the constitutively active polypeptide. The invention also provides for use of tissue-specific promoters derived from viruses including, e.g., the tobamovirus subgenomic promoter (Kumagai, *Proc. Natl. Acad. Sci. USA* 92:1679-1683, 1995); the rice tungro bacilliform virus (RTBV), which replicates only in phloem cells in infected rice plants, with its promoter which drives strong phloem-specific reporter gene expression; the cassava vein mosaic virus (CVMV) promoter, with highest activity in vascular elements, in leaf mesophyll cells, and in root tips (Verdaguer, *Plant Mol. Biol.* 31:1129-1139, 1996).

A vector comprising nucleic acid sequences encoding the polypeptide will typically comprise a marker gene that confers a selectable phenotype on the cell to which it is introduced. Such markers are known. For example, the marker may encode antibiotic resistance, such as resistance to kanamycin, G418, bleomycin, hygromycin, and the like.

Nucleic acid sequences encoding the polypeptide of the invention are expressed recombinantly in plant cells as described. As appreciated by one of skill in the art, expression constructs can be designed taking into account such properties as codon usage frequencies of the plant in which the nucleic acid encoding the polypeptide is to be expressed. Codon usage frequencies can be tabulated using known methods (see, e.g., Nakamura et al. *Nucl. Acids Res.* 28:292, 2000). Codon usage frequency tables are available in the art (e.g., from the Codon Usage Database at the internet site at kazusa.or.jp/codon/.)

Additional sequence modifications may be made that are also known to enhance gene expression in a plant. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence may also be modified to avoid predicted hairpin secondary mRNA structures.

Production of Modified Cells or Transgenic Plants

In some embodiments, the modified eukaryotic cell is a plant cell. Techniques for genetically modifying eukaryotic cells, such as plant, animal and fungal cells are well known to those skilled in the art. For example, U.S. Provisional Patent Application Ser. No. 61/676,811 teaches such methods for yeast.

In some embodiments, the plant is a grass plant. In some embodiments, the plant of plant cell is *Arabidopsis*, poplar, eucalyptus, rice, corn, cotton, switchgrass, sorghum, millet, miscanthus, sugarcane, pine, alfalfa, wheat, soy, barley, turfgrass, tobacco, hemp, bamboo, rape, sunflower, willow, or *Brachypodium*

The present invention provides for transgenic plants comprising recombinant expression cassettes either for expressing the polypeptide. It should be recognized that the term "transgenic plants" as used here encompasses the plant or plant cell in which the expression cassette is introduced as well as progeny of such plants or plant cells that contain the expression cassette, including the progeny that have the expression cassette stably integrated in a chromosome.

Once an expression cassette comprising a polynucleotide encoding the polypeptide has been constructed, standard techniques may be used to introduce the polynucleotide into a plant in order to modify gene expression. See, e.g., protocols described in Ammirato et al. (1984) Handbook of Plant Cell Culture—Crop Species. Macmillan Publ. Co. Shimamoto et al. (1989) Nature 338:274-276; Fromm et al. (1990) Bio/Technology 8:833-839; and Vasil et al. (1990) Bio/Technology 8:429-434.

Transformation and regeneration of plants is known in the art, and the selection of the most appropriate transformation technique will be determined by the practitioner. Suitable methods may include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium tumeficiens* mediated transformation. Transformation means introducing a nucleotide sequence in a plant in a manner to cause stable or transient expression of the sequence. Examples of these methods in various plants include: U.S. Pat. Nos. 5,571,706; 5,677,175; 5,510,471; 5,750,386; 5,597,945; 5,589,615; 5,750,871; 5,268,526; 5,780,708; 5,538,880; 5,773,269; 5,736,369 and 5,610,042.

Transformed plant cells derived by any of the above transformation techniques can be cultured to regenerate a whole plant that possesses the transformed genotype and thus the desired phenotype such as enhanced drought-resistance. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985. Regeneration can also be obtained from plant callus, explants, organs, or parts thereof. Such regeneration techniques are described generally, e.g., in Klee et al. *Ann. Rev. of Plant Phys.* 38:467-486, 1987.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

The expression constructs of the invention can be used to increase the sugar content of cell walls of essentially any plant. The plant may be a monocotyledonous plant or a dicotyledonous plant. In some embodiments of the invention, the plant is a green field plant. In some embodiments, the plant is a gymnosperm or conifer. Thus, the invention has use over a broad range of plants, including species from the genera *Asparagus, Atropa, Avena, Brassica, Cannabis, Citrus, Citrullus, Camelina, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malus, Manihot, Majorana, Medicago, Nicotiana, Oryza, Panieum, Pannesetum, Persea, Pisum, Pyrus, Prunus, Raphanus, Secale, Senecio, Sinapis, Solanum, Sorghum, Trigonella, Triticum, Vitis, Vigna*, and, *Zea*. In some embodiments, the plant is corn, switchgrass, sorghum, miscanthus, sugarcane, poplar, pine, wheat, rice, soy, cotton, barley, turf grass, tobacco, potato, bamboo, rape, sugar beet, sunflower, willow, and eucalyptus. In further embodiments, the plant is reed canarygrass (*Phalaris arundinacea*), *Miscanthus* x *giganteus, Miscanthus* sp., sericea lespedeza (*Lespedeza cuneata*), millet, ryegrass (*Lolium multiflorum, Lolium* sp.), timothy, Kochia (*Kochia scoparia*), forage soybeans, alfalfa, clover, sunn hemp, kenaf, bahiagrass, bermudagrass, dallisgrass, pangolagrass, big bluestem, indiangrass, fescue (*Festuca* sp.), *Dactylis* sp., *Brachypodium distachyon*, smooth bromegrass, orchardgrass, or Kentucky bluegrass among others. In some embodiments, the plant is an ornamental plant. In some embodiments, the plant is a grass plant. In some embodiment, the plant is a vegetable- or fruit-producing plant. In some embodiments, the plant is a plant that is suitable for generating biomass, including plants as noted above, e.g., *Arabidopsis*, poplar, eucalyptus, rice, corn, switchgrass, sorghum, millet, miscanthus, sugarcane, pine, alfalfa, wheat, soy, barley, turfgrass, tobacco, hemp, bamboo, rape, sunflower, willow, *Jatropha*, and *Brachypodium*.

In some embodiments, the plant into which the expression construct comprising a nucleic acid sequence that encodes the polypeptide is introduced is the same species of plant from which the mutant IRX10 sequence, and/or the promoter driving expression of the mutant IRX10 sequence, is obtained. In some embodiments, the plant into which the expression construct is introduced is a different species of plant compared to the species from which the mutant IRX10 and/or promoter sequence was obtained.

Plants that overexpress the mutant IRX10 can be identified using any known assay, including analysis of RNA, protein, or xylan composition. The xylan levels can be determined directly or indirectly, wherein such methods are well known in the art.

An expression cassette comprising a polynucleotide encoding the polypeptide operably linked to a promoter, as described herein, can be expressed in various kinds of plants. The plant may be a monocotyledonous plant or a dicotyledonous plant. In some embodiments of the invention, the plant is a green field plant. In some embodiments, the plant is a gymnosperm or conifer.

In some embodiments, the plant is a plant that is suitable for generating biomass. Examples of suitable plants include, but are not limited to, *Arabidopsis*, poplar, eucalyptus, rice, corn, switchgrass, sorghum, millet, miscanthus, sugarcane, pine, alfalfa, wheat, soy, barley, turfgrass, tobacco, hemp, bamboo, rape, sunflower, willow, *Jatropha*, and *Brachypodium*.

In some embodiments, the plant into which the expression cassette is introduced is the same species of plant as the promoter and/or as the polynucleotide encoding the polypeptide or transcription factor (e.g., a vessel-specific promoter and/or transcription factor from *Arabidopsis* is expressed in an *Arabidopsis* plant). In some embodiments, the plant into which the expression cassette is introduced is a different species of plant than the promoter and/or than the polynucleotide encoding the polypeptide or transcription factor (e.g., a vessel-specific promoter and/or transcription factor from *Arabidopsis* is expressed in a poplar plant). See, e.g., McCarthy et al., *Plant Cell Physiol.* 51:1084-90 (2010); and Zhong et al., *Plant Physiol.* 152:1044-55 (2010).

Methods of enzymatic saccharification are also known in the art. Briefly, plants or plant biomass material (e.g., leaves and stems) are optionally pre-treated with hot water, dilute acid, alkali, or ionic liquid followed by enzymatic saccharification using a mixture of cellulases and hemicellulases and pectinases in buffer and incubation of the plants or plant biomass material with the enzymatic mixture. Following incubation, the yield of the saccharification reaction can be readily determined by measuring the amount of reducing sugar released, using a standard method for sugar detection, e.g. the dinitrosalicylic acid method well known to those skilled in the art. Plants engineered in accordance with the invention provide a higher sugar yield as compared to wild-type plants.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

EXAMPLE 1

Dominant Suppression of Xylan Biosynthesis Using IRX10

Potential catalytic residues in the xylan biosynthetic enzyme IRX10 are identified and mutated. The overexpression of the mutated IRX10 out competes the native form of the enzyme resulting in the suppression of the biosynthesis of the polymer.

Figures 2, 3:
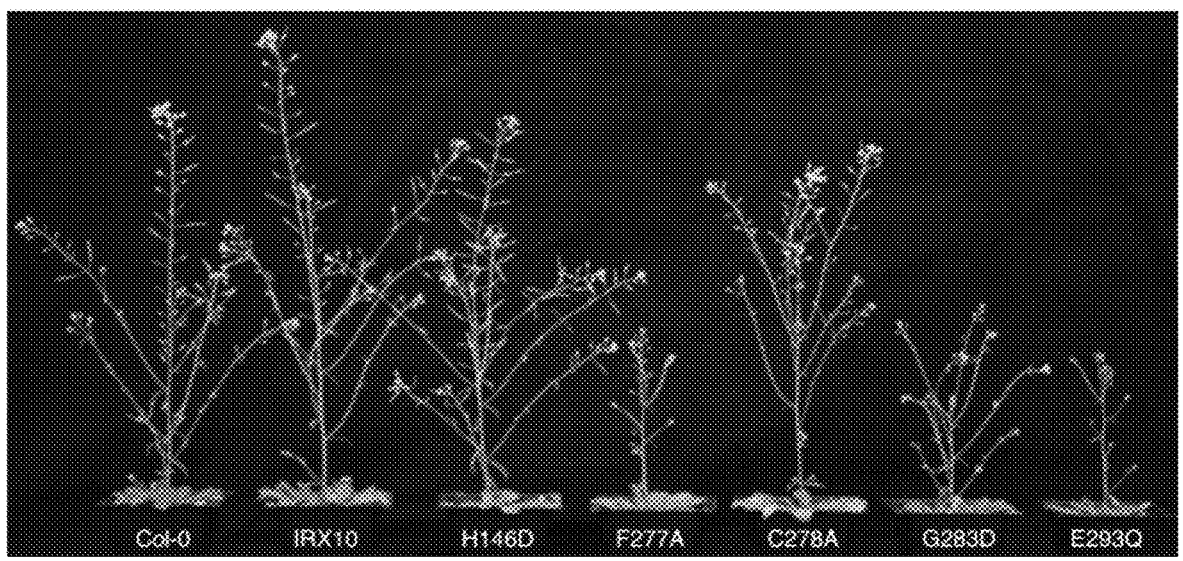
FIG. 2 shows a comparison the amino acid sequences between *Arabidopsis* IRX10, IRX10-L, OsIRX10, PpIRX10, and HsEXO1 (SEQ ID NOs:1 to 5, respectively). IRX10 is well conserved within diverse homologs, including human EXO1. Conserved amino acid residues are indicated.
FIG. 3 shows that mutant plants overexpressing the mutant IRX10 have a phenotype consistent with reduced xylan.

FIG. 2 shows a comparison the amino acid sequences between *Arabidopsis* IRX10, IRX10-L, OsIRX10, PpIRX10, and HsEXO1. IRX10 is well conserved within diverse homologs, including human EXO1. The indicated IRX10 mutants shown in FIG. 2 are generated and are overexpressed in plants. FIG. 3 shows that the mutant plants overexpressing the mutant IRX10s have a phenotype consistent with reduced xylan.

Figure 4:
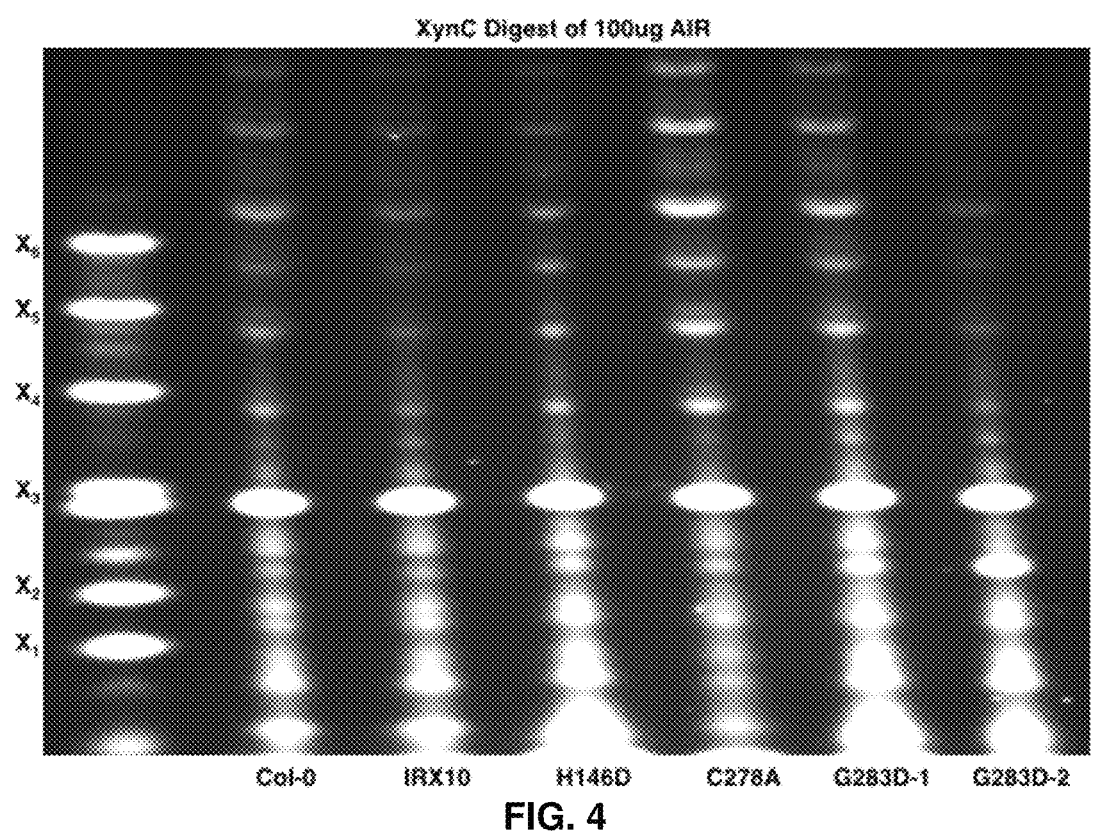
FIG. 4 shows that suppressors may alter the substitution pattern of the xylan backbone.
Figure 5:
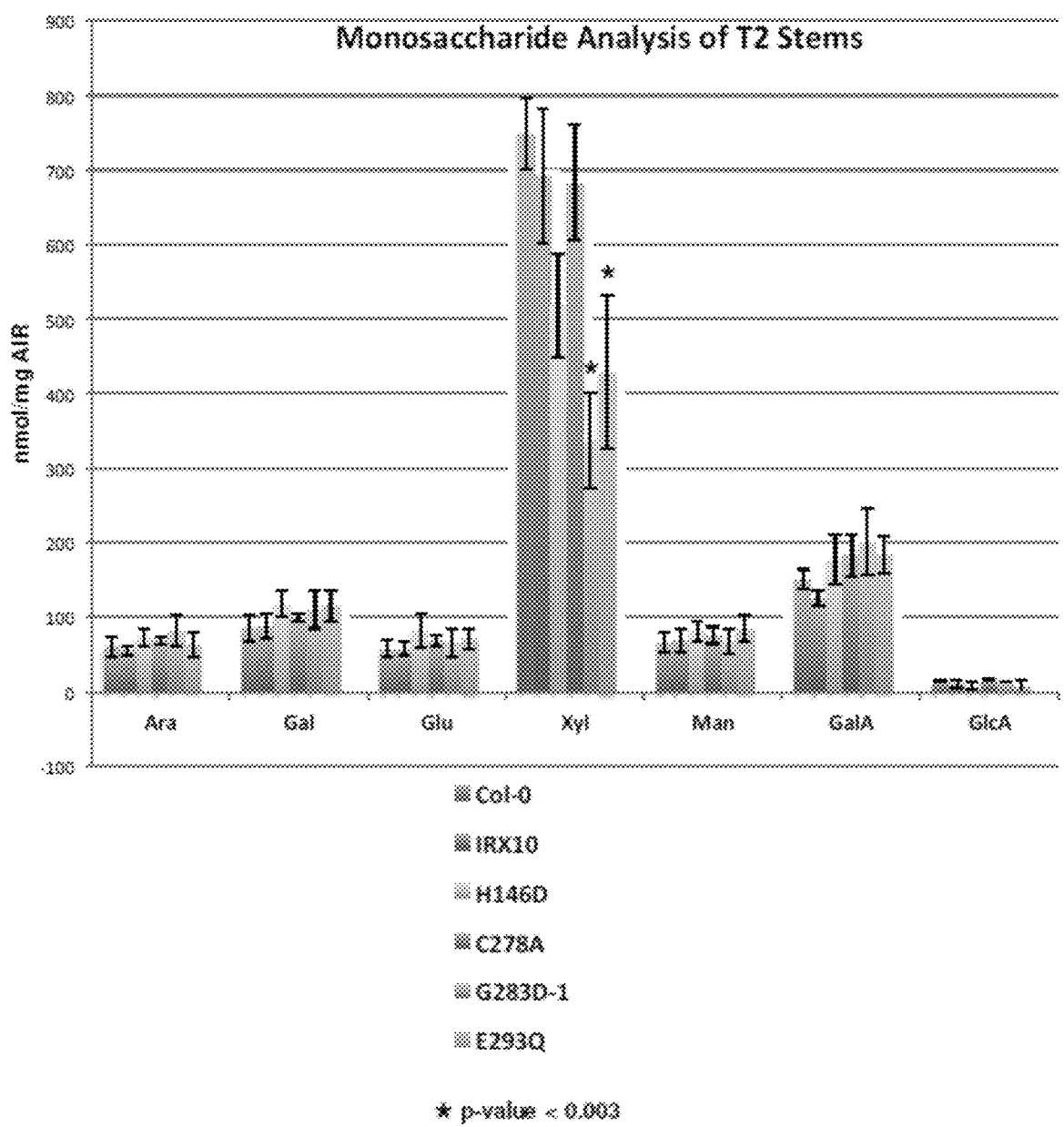
FIG. 5 shows the monosaccharide analysis of T2 stems.

Cell wall material from the plants in FIG. 3 are isolated and digested with Xylanase C, an enzyme that cleaves xylan specifically at glucuronic acid substitutions. The digestion products are then fluorescently labelled and separated by size. FIG. 4 shows the distribution of glucuronic acid residues along the xylan chain. FIG. 4 shows that suppressors may alter the substitution pattern of the xylan backbone. Cell wall material from the basal stem of at least 3 biological replicates is fully hydrolyzed with TFA and the monosaccharides separated and quantified via HPAEC. FIG. 5 shows the monosaccharide analysis of T2 stems. The results indicate that the biosynthesis of xylan is reduced in the plants with the mutant IRX10.

Figure 6:
FIG. 6 shows a construct for restricting the expression of the suppressor in the plant vessels.

To eliminate the yield reduction associated with reduced xylan, expression of the suppressor is restricted specifically to the vessels. This can be accomplished by expressing the Cre recombinase under the vessel specific promoter pVND7. Cre recognizes cognate loxP sites, looping out any sequence between the sites from the genome. FIG. 6 shows a construct for restricting the expression of the suppressor in the plant vessels.

The results demonstrate the following: IRX10 is at least 70% conserved in all land plants and potential catalytic residues can be identified. Mutations in some of the residues chosen are able to dominantly suppress xylan biosynthesis and reduce the amount of xylose in the plant by as much as about 55%. The mutation G283D, is the same mutation linked to cancer in the human homolog EXO1, exhibits significant suppression.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A non-naturally occurring nucleic acid encoding a mutant polypeptide operably linked to a heterologous promoter, wherein the mutant polypeptide exhibits dominant suppression of the naturally occurring IRX10 polypeptide as set forth in SEQ ID NO: 1, wherein the mutant polypeptide comprises one or more of the following mutations in the amino acid sequence as set forth in SEQ ID NO: 1: the histidine at position 146 of SEQ ID NO: 1 is substituted with the aspartate amino acid residue, the cysteine at position 278 of SEQ ID NO: 1 is substituted with the alanine amino acid residue, the glycine at position 283 of SEQ ID NO: 1 is substituted with the aspartate amino acid residue, and the glutamic acid at position 293 of SEQ ID NO: 1 is substituted with the glutamine amino acid residue, and wherein overexpression of said mutant polypeptide in a plant reduces xylan biosynthesis in said plant.

2. A host cell comprising the non-naturally occurring nucleic acid of claim 1.

3. A plant transformed with the non-naturally occurring nucleic acid of claim 1.

4. A method of reducing xylan biosynthesis in a plant, comprising: (a) transforming a plant with the non-naturally occurring nucleic acid of claim 2, and (b) culturing or growing the transformed plant for overexpression of the non-naturally occurring nucleic acid encoding the mutant polypeptide in said transformed plant to reduce biosynthesis of xylan in the transformed plant as compared to a corresponding control plant of the same plant species lacking the non-naturally occurring nucleic acid and grown under similar growth conditions.

5. The method of claim 4, wherein the heterologous promoter is a constitutive promoter.

6. The method of claim 4, wherein the heterologous promoter is an inducible promoter.

7. The method of claim 4, wherein the heterologous promoter is a tissue specific promoter.

8. The method of claim 7, wherein the tissue specific promoter is a vessel specific promoter.

9. The method of claim 7, wherein the tissue specific promoter is a secondary wall specific promoter.

10. The method of claim 4, wherein the glutamic acid at position 293 of SEQ ID NO: 1 is substituted with the glutamine amino acid residue in the mutant polypeptide.

11. The non-naturally occurring nucleic acid of claim 1, wherein the glycine at position 283 of SEQ ID NO: 1 is substituted with the aspartate amino acid residue in the mutant polypeptide.

* * * * *

```
                         SEQUENCE LISTING

<160> NUMBER OF SEQ ID NOS: 5

<210> SEQ ID NO 1
<211> LENGTH: 412
<212> TYPE: PRT
<213> ORGANISM: Arabidopsis thaliana

<400> SEQUENCE: 1

Met Lys Ile His Ser Cys Leu Ser Ala Ile Leu Leu Phe Leu Phe Phe
1               5                   10                  15

Ser Ala Ser Ala Lys Gln Asn Val Arg Thr Glu Arg Ile Ser Gly
                20                  25                  30

Ser Ala Gly Asp Val Leu Glu Asp Asp Pro Val Gly Lys Leu Lys Val
                35                  40                  45

Tyr Val Tyr Glu Leu Pro Ser Lys Tyr Asn Lys Lys Leu Leu Gln Lys
    50                  55                  60

Asp Pro Arg Cys Leu Thr His Met Phe Ala Ala Glu Ile Phe Met His
65                  70                  75                  80

Arg Phe Leu Leu Ser Ser Pro Val Arg Thr Arg Asn Pro Asp Glu Ala
                85                  90                  95

Asp Trp Phe Tyr Thr Pro Ile Tyr Pro Thr Cys Asp Leu Thr Pro Thr
                100                 105                 110

Gly Leu Pro Leu Pro Phe Lys Ser Pro Arg Met Met Arg Ser Ser Ile
                115                 120                 125

Gln Leu Ile Ser Ser Asn Trp Pro Tyr Trp Asn Arg Thr Glu Gly Ala
            130                 135                 140

Asp His Phe Phe Val Val Pro His Asp Phe Gly Ala Cys Phe His Tyr
145                 150                 155                 160

Gln Glu Glu Lys Ala Ile Glu Arg Gly Ile Leu Pro Leu Leu Gln Arg
                165                 170                 175

Ala Thr Leu Val Gln Thr Phe Gly Gln Arg Asn His Val Cys Leu Asp
                180                 185                 190

Glu Gly Ser Ile Thr Ile Pro Pro Phe Ala Pro Pro Gln Lys Met Gln
            195                 200                 205

Ala His Phe Ile Pro Pro Asp Ile Pro Arg Ser Ile Phe Val Tyr Phe
    210                 215                 220

Arg Gly Leu Phe Tyr Asp Val Asn Asn Asp Pro Glu Gly Gly Tyr Tyr
225                 230                 235                 240

Ala Arg Gly Ala Arg Ala Ala Val Trp Glu Asn Phe Lys Asn Asn Pro
                245                 250                 255

Leu Phe Asp Ile Ser Thr Asp His Pro Thr Thr Tyr Tyr Glu Asp Met
            260                 265                 270

Gln Arg Ala Ile Phe Cys Leu Cys Pro Leu Gly Trp Ala Pro Trp Ser
    275                 280                 285

Pro Arg Leu Val Glu Ala Val Val Phe Gly Cys Ile Pro Val Ile Ile
    290                 295                 300

Ala Asp Asp Ile Val Leu Pro Phe Ala Asp Ala Ile Pro Trp Glu Glu
305                 310                 315                 320
```

```
Ile Gly Val Phe Val Ala Glu Lys Asp Val Pro Glu Leu Asp Thr Ile
                325                 330                 335

Leu Thr Ser Ile Pro Thr Glu Val Ile Leu Arg Lys Gln Arg Leu Leu
                340                 345                 350

Ala Asn Pro Ser Met Lys Arg Ala Met Leu Phe Pro Gln Pro Ala Gln
                355                 360                 365

Pro Gly Asp Ala Phe His Gln Ile Leu Asn Gly Leu Ala Arg Lys Leu
                370                 375                 380

Pro His Asp Lys Ser Ile Tyr Leu Lys Thr Gly Glu Lys Ala Leu Asn
385                 390                 395                 400

Trp Thr Ala Gly Pro Val Ala Asp Leu Lys Pro Trp
                405                 410

<210> SEQ ID NO 2
<211> LENGTH: 415
<212> TYPE: PRT
<213> ORGANISM: Arabidopsis thaliana

<400> SEQUENCE: 2

Met Lys Leu Ser Ser Cys Val Leu Ile Phe Leu Leu Cys Asn Thr Phe
1               5                   10                  15

Ser Ser Ile Ser Ala Phe Arg Leu Ser Arg Ser Gln Pro Thr Glu Arg
                20                  25                  30

Ile Ser Gly Ser Ala Gly Asp Val Leu Glu Asp Pro Val Gly Arg
                35                  40                  45

Leu Lys Val Phe Val Tyr Glu Leu Pro Ser Lys Tyr Asn Lys Lys Ile
    50                  55                  60

Leu Gln Lys Asp Pro Arg Cys Leu Asn His Met Phe Ala Ala Glu Ile
65                  70                  75                  80

Tyr Met Gln Arg Phe Leu Leu Ser Ser Pro Val Arg Thr Leu Asn Pro
                85                  90                  95

Glu Glu Ala Asp Trp Phe Tyr Val Pro Val Tyr Thr Thr Cys Asp Leu
                100                 105                 110

Thr Pro Asn Gly Leu Pro Leu Pro Phe Lys Ser Pro Arg Met Met Arg
                115                 120                 125

Ser Ala Ile Gln Leu Ile Ala Ser Asn Trp Pro Tyr Trp Asn Arg Thr
    130                 135                 140

Glu Gly Ala Asp His Phe Val Val Pro His Asp Phe Gly Ala Cys
145                 150                 155                 160

Phe His Tyr Gln Glu Glu Lys Ala Ile Gly Arg Gly Ile Leu Pro Leu
                165                 170                 175

Leu Gln Arg Ala Thr Leu Val Gln Thr Phe Gly Gln Arg Asn His Val
                180                 185                 190

Cys Leu Lys Glu Gly Ser Ile Thr Val Pro Pro Tyr Ala Pro Pro Gln
    195                 200                 205

Lys Met Gln Ser His Leu Ile Pro Glu Lys Thr Pro Arg Ser Ile Phe
210                 215                 220

Val Tyr Phe Arg Gly Leu Phe Tyr Asp Val Gly Asn Asp Pro Glu Gly
225                 230                 235                 240

Gly Tyr Tyr Ala Arg Gly Ala Arg Ala Ala Val Trp Glu Asn Phe Lys
                245                 250                 255

Asp Asn Pro Leu Phe Asp Ile Ser Thr Glu His Pro Thr Thr Tyr Tyr
                260                 265                 270

Glu Asp Met Gln Arg Ala Ile Phe Cys Leu Cys Pro Leu Gly Trp Ala
```

```
            275                 280                 285
Pro Trp Ser Pro Arg Leu Val Glu Ala Val Ile Phe Gly Cys Ile Pro
        290                 295                 300

Val Ile Ile Ala Asp Asp Ile Val Leu Pro Phe Ala Asp Ala Ile Pro
305                 310                 315                 320

Trp Glu Asp Ile Gly Val Phe Val Asp Glu Lys Asp Val Pro Tyr Leu
                325                 330                 335

Asp Thr Ile Leu Thr Ser Ile Pro Pro Glu Val Ile Leu Arg Lys Gln
            340                 345                 350

Arg Leu Leu Ala Asn Pro Ser Met Lys Gln Ala Met Leu Phe Pro Gln
        355                 360                 365

Pro Ala Gln Pro Gly Asp Ala Phe His Gln Val Leu Asn Gly Leu Ala
370                 375                 380

Arg Lys Leu Pro His Glu Arg Ser Val Tyr Leu Arg Pro Gly Glu Lys
385                 390                 395                 400

Leu Leu Asn Trp Thr Ala Gly Pro Val Ala Asp Leu Lys Pro Trp
                405                 410                 415

<210> SEQ ID NO 3
<211> LENGTH: 417
<212> TYPE: PRT
<213> ORGANISM: Oryza sativa

<400> SEQUENCE: 3

Met Arg Arg Trp Val Leu Ala Ile Ala Ile Leu Ala Ala Ala Val Cys
1               5                   10                  15

Phe Phe Leu Gly Ala Gln Ala Gln Glu Val Arg Gln Gly His Gln Thr
                20                  25                  30

Glu Arg Ile Ser Gly Ser Ala Gly Asp Val Leu Glu Asp Asp Pro Val
            35                  40                  45

Gly Arg Leu Lys Val Tyr Val Tyr Asp Leu Pro Ser Lys Tyr Asn Lys
        50                  55                  60

Lys Leu Leu Lys Lys Asp Pro Arg Cys Leu Asn His Met Phe Ala Ala
65                  70                  75                  80

Glu Ile Phe Met His Arg Phe Leu Leu Ser Ser Ala Val Arg Thr Phe
                85                  90                  95

Asn Pro Glu Glu Ala Asp Trp Phe Tyr Thr Pro Val Tyr Thr Thr Cys
                100                 105                 110

Asp Leu Thr Pro Ser Gly Leu Pro Leu Pro Phe Lys Ser Pro Arg Met
            115                 120                 125

Met Arg Ser Ala Ile Glu Leu Ile Ala Thr Asn Trp Pro Tyr Trp Asn
        130                 135                 140

Arg Ser Glu Gly Ala Asp His Phe Phe Val Thr Pro His Asp Phe Gly
145                 150                 155                 160

Ala Cys Phe His Tyr Gln Glu Glu Lys Ala Ile Gly Arg Gly Ile Leu
                165                 170                 175

Pro Leu Leu Gln Arg Ala Thr Leu Val Gln Thr Phe Gly Gln Lys Asn
            180                 185                 190

His Val Cys Leu Lys Asp Gly Ser Ile Thr Ile Pro Pro Tyr Ala Pro
        195                 200                 205

Pro Gln Lys Met Gln Ala His Leu Ile Pro Pro Asp Thr Pro Arg Ser
210                 215                 220

Ile Phe Val Tyr Phe Arg Gly Leu Phe Tyr Asp Thr Ser Asn Asp Pro
225                 230                 235                 240
```

-continued

Glu Gly Gly Tyr Tyr Ala Arg Gly Ala Arg Ala Ser Val Trp Glu Asn
                245                 250                 255

Phe Lys Asn Asn Pro Leu Phe Asp Ile Ser Thr Asp His Pro Pro Thr
            260                 265                 270

Tyr Tyr Glu Asp Met Gln Arg Ser Val Phe Cys Leu Cys Pro Leu Gly
        275                 280                 285

Trp Ala Pro Trp Ser Pro Arg Leu Val Glu Ala Val Val Phe Gly Cys
290                 295                 300

Ile Pro Val Ile Ile Ala Asp Asp Ile Val Leu Pro Phe Ala Asp Ala
305                 310                 315                 320

Ile Pro Trp Glu Glu Ile Gly Val Phe Val Ala Glu Glu Asp Val Pro
                325                 330                 335

Lys Leu Asp Ser Ile Leu Thr Ser Ile Pro Thr Asp Val Ile Leu Arg
            340                 345                 350

Lys Gln Arg Leu Leu Ala Asn Pro Ser Met Lys Gln Ala Met Leu Phe
        355                 360                 365

Pro Gln Pro Ala Gln Ala Gly Asp Ala Phe His Gln Ile Leu Asn Gly
370                 375                 380

Leu Ala Arg Lys Leu Pro His Gly Glu Asn Val Phe Leu Lys Pro Gly
385                 390                 395                 400

Glu Arg Ala Leu Asn Trp Thr Ala Gly Pro Val Gly Asp Leu Lys Pro
                405                 410                 415

Trp

<210> SEQ ID NO 4
<211> LENGTH: 449
<212> TYPE: PRT
<213> ORGANISM: Physcomitrella patens

<400> SEQUENCE: 4

Met Glu His Pro Leu Glu Cys Ala Asp Ser Cys Ser Leu Ala Met Ser
1               5                   10                  15

Trp Phe Cys Asn Lys Lys Cys Arg Gly Trp Gly Leu Met Lys Arg Thr
            20                  25                  30

Val Val Ala Ser Gly Leu Arg Ser Val Val Leu Leu Leu Phe Ile
        35                  40                  45

Tyr Phe Val Gln Asp Val Thr Ala Glu Met Gly His Gln Arg Ile Ser
    50                  55                  60

Gly Ser Ala Gly Asp Val Leu Glu Asp Asn Pro Val Gly Arg Leu Lys
65                  70                  75                  80

Val Phe Ile Tyr Asp Ile Pro Ser Lys Tyr Asn Thr Asp Trp Leu Lys
                85                  90                  95

Lys Asp Pro Arg Cys Leu Thr His Met Phe Ala Val Glu Glu Tyr Leu
            100                 105                 110

His Asp Phe Leu Thr Glu Ser Pro Val Arg Thr Leu Asn Pro Glu Glu
        115                 120                 125

Ala Asp Trp Phe Tyr Thr Pro Val Tyr Thr Thr Cys Asp Leu Thr Pro
    130                 135                 140

Asn Gly Leu Pro Leu Pro Phe Lys Ser Pro Arg Val Met Arg Ser Ala
145                 150                 155                 160

Ile Ser Tyr Ile Ser Ser His Trp Pro Tyr Trp Asn Arg Thr Asp Gly
                165                 170                 175

Ala Asp His Phe Phe Val Val Pro His Asp Ala Ala Cys Phe His
            180                 185                 190

```
Tyr Gln Glu Glu Lys Ala Ile Glu Arg Gly Ile Leu Pro Leu Leu Lys
            195                 200                 205

Arg Ala Thr Leu Ile Gln Thr Phe Gly Gln Asn His His Val Cys Leu
210                 215                 220

Lys Glu Asp Ser Ile Val Ile Pro Pro Tyr Ala Pro Pro Glu Arg Met
225                 230                 235                 240

Gln Thr Arg Leu Asn Pro Pro Ser Thr Pro Arg Ser Ile Phe Ala Tyr
            245                 250                 255

Phe Arg Gly Leu Phe Tyr Asp Pro Gly Asn Asp Pro Glu Gly Gly Tyr
            260                 265                 270

Tyr Ala Arg Gly Ala Arg Ala Ala Ile Trp Glu Asn Phe Lys Asp Asn
            275                 280                 285

Pro Leu Phe Asp Ile Ser Thr Glu His Pro Ala Thr Tyr Tyr Glu Asp
            290                 295                 300

Met Gln Arg Ala Ile Phe Cys Leu Cys Pro Leu Gly Trp Ala Pro Trp
305                 310                 315                 320

Ser Pro Arg Leu Val Glu Gly Val Ile Phe Gly Cys Ile Pro Val Ile
            325                 330                 335

Ile Ala Asp Asp Ile Val Leu Pro Phe Ala Asp Ala Ile Pro Trp Glu
            340                 345                 350

Lys Ile Gly Val Phe Val Glu Glu Lys Asp Val Pro Ile Leu Asp Lys
            355                 360                 365

Ile Leu Cys Thr Ile Asn His Glu Glu Val Leu Glu Lys Gln Arg Leu
            370                 375                 380

Leu Ala Asn Pro Ala Met Lys Gln Ala Met Leu Phe Pro Arg Pro Ala
385                 390                 395                 400

Lys Pro Gly Asp Ala Phe His Gln Ile Leu Asn Gly Leu Ala Arg Lys
            405                 410                 415

Leu Pro His Asp Pro Ser Ile Tyr Leu Gln Pro Gly Gln Ser Phe Leu
            420                 425                 430

Asn Trp Thr Glu Gly Pro Pro Gly Asp Leu Tyr Pro Trp Gly Asn Asp
            435                 440                 445

Leu

<210> SEQ ID NO 5
<211> LENGTH: 746
<212> TYPE: PRT
<213> ORGANISM: Homo sapiens

<400> SEQUENCE: 5

Met Gln Ala Lys Lys Arg Tyr Phe Ile Leu Ser Ala Gly Ser Cys
1               5                   10                  15

Leu Ala Leu Leu Phe Tyr Phe Gly Gly Leu Gln Phe Arg Ala Ser Arg
            20                  25                  30

Ser His Ser Arg Arg Glu Glu His Ser Gly Arg Asn Gly Leu His His
            35                  40                  45

Pro Ser Pro Asp His Phe Trp Pro Arg Phe Pro Asp Ala Leu Arg Pro
            50                  55                  60

Phe Val Pro Trp Asp Gln Leu Glu Asn Glu Asp Ser Ser Val His Ile
65                  70                  75                  80

Ser Pro Arg Gln Lys Arg Asp Ala Asn Ser Ser Ile Tyr Lys Gly Lys
            85                  90                  95

Lys Cys Arg Met Glu Ser Cys Phe Asp Phe Thr Leu Cys Lys Lys Asn
            100                 105                 110
```

```
Gly Phe Lys Val Tyr Val Tyr Pro Gln Gln Lys Gly Lys Ile Ala
            115                 120                 125
Glu Ser Tyr Gln Asn Ile Leu Ala Ala Ile Glu Gly Ser Arg Phe Tyr
            130                 135                 140
Thr Ser Asp Pro Ser Gln Ala Cys Leu Phe Val Leu Ser Leu Asp Thr
145                 150                 155                 160
Leu Asp Arg Asp Gln Leu Ser Pro Gln Tyr Val His Asn Leu Arg Ser
            165                 170                 175
Lys Val Gln Ser Leu His Leu Trp Asn Gly Arg Asn His Leu Ile
            180                 185                 190
Phe Asn Leu Tyr Ser Gly Thr Trp Pro Asp Tyr Thr Glu Asp Val Gly
            195                 200                 205
Phe Asp Ile Gly Gln Ala Met Leu Ala Lys Ala Ser Ile Ser Thr Glu
            210                 215                 220
Asn Phe Arg Pro Asn Phe Asp Val Ser Ile Pro Leu Phe Ser Lys Asp
225                 230                 235                 240
His Pro Arg Thr Gly Gly Glu Arg Gly Phe Leu Lys Phe Asn Thr Ile
            245                 250                 255
Pro Pro Leu Arg Lys Tyr Met Leu Val Phe Lys Gly Lys Arg Tyr Leu
            260                 265                 270
Thr Gly Ile Gly Ser Asp Thr Arg Asn Ala Leu Tyr His Val His Asn
            275                 280                 285
Gly Glu Asp Val Val Leu Leu Thr Thr Cys Lys His Gly Lys Asp Trp
            290                 295                 300
Gln Lys His Lys Asp Ser Arg Cys Asp Arg Asp Asn Thr Glu Tyr Glu
305                 310                 315                 320
Lys Tyr Asp Tyr Arg Glu Met Leu His Asn Ala Thr Phe Cys Leu Val
            325                 330                 335
Pro Arg Gly Arg Arg Leu Gly Ser Phe Arg Phe Leu Glu Ala Leu Gln
            340                 345                 350
Ala Ala Cys Val Pro Val Met Leu Ser Asn Gly Trp Glu Leu Pro Phe
            355                 360                 365
Ser Glu Val Ile Asn Trp Asn Gln Ala Ala Val Ile Gly Asp Glu Arg
            370                 375                 380
Leu Leu Leu Gln Ile Pro Ser Thr Ile Arg Ser Ile His Gln Asp Lys
385                 390                 395                 400
Ile Leu Ala Leu Arg Gln Gln Thr Gln Phe Leu Trp Glu Ala Tyr Phe
            405                 410                 415
Ser Ser Val Glu Lys Ile Val Leu Thr Thr Leu Glu Ile Ile Gln Asp
            420                 425                 430
Arg Ile Phe Lys His Ile Ser Arg Asn Ser Leu Ile Trp Asn Lys His
            435                 440                 445
Pro Gly Gly Leu Phe Val Leu Pro Gln Tyr Ser Ser Tyr Leu Gly Asp
450                 455                 460
Phe Pro Tyr Tyr Tyr Ala Asn Leu Gly Leu Lys Pro Pro Ser Lys Phe
465                 470                 475                 480
Thr Ala Val Ile His Ala Val Thr Pro Leu Val Ser Gln Ser Gln Pro
            485                 490                 495
Val Leu Lys Leu Leu Val Ala Ala Lys Ser Gln Tyr Cys Ala Gln
            500                 505                 510
Ile Ile Val Leu Trp Asn Cys Asp Lys Pro Leu Pro Ala Lys His Arg
            515                 520                 525
Trp Pro Ala Thr Ala Val Pro Val Val Val Ile Glu Gly Glu Ser Lys
```

-continued

```
                530                 535                 540
Val Met Ser Ser Arg Phe Leu Pro Tyr Asp Asn Ile Ile Thr Asp Ala
545                 550                 555                 560

Val Leu Ser Leu Asp Glu Asp Thr Val Leu Ser Thr Thr Glu Val Asp
                565                 570                 575

Phe Ala Phe Thr Val Trp Gln Ser Phe Pro Glu Arg Ile Val Gly Tyr
                580                 585                 590

Pro Ala Arg Ser His Phe Trp Asp Asn Ser Lys Glu Arg Trp Gly Tyr
                595                 600                 605

Thr Ser Lys Trp Thr Asn Asp Tyr Ser Met Val Leu Thr Gly Ala Ala
                610                 615                 620

Ile Tyr His Lys Tyr Tyr His Tyr Leu Tyr Ser His Tyr Leu Pro Ala
625                 630                 635                 640

Ser Leu Lys Asn Met Val Asp Gln Leu Ala Asn Cys Glu Asp Ile Leu
                645                 650                 655

Met Asn Phe Leu Val Ser Ala Val Thr Lys Leu Pro Pro Ile Lys Val
                660                 665                 670

Thr Gln Lys Lys Gln Tyr Lys Glu Thr Met Met Gly Gln Thr Ser Arg
                675                 680                 685

Ala Ser Arg Trp Ala Asp Pro Asp His Phe Ala Gln Arg Gln Ser Cys
                690                 695                 700

Met Asn Thr Phe Ala Ser Trp Phe Gly Tyr Met Pro Leu Ile His Ser
705                 710                 715                 720

Gln Met Arg Leu Asp Pro Val Leu Phe Lys Asp Gln Val Ser Ile Leu
                725                 730                 735

Arg Lys Lys Tyr Arg Asp Ile Glu Arg Leu
                740                 745
```